US009282887B2

(12) United States Patent
Cense et al.

(10) Patent No.: US 9,282,887 B2
(45) Date of Patent: Mar. 15, 2016

(54) THREE-DIMENSIONAL RETINA IMAGE GENERATOR (71) Applicant: UTSUNOMIYA UNIVERSITY, Utsunomiya-shi, Tochigi (JP)

(72) Inventors: Abraham J. Cense, Utsunomiya (JP); Roy de Kinkelder, Zenderen (NL)

(73) Assignee: UTSUNOMIYA UNIVERSITY, Utsunomiya-shi, Tochigi (JP)

( * ) Notice: Subject to any disclaimer, the term of this patent is extended or adjusted under 35 U.S.C. 154(b) by 0 days.

(21) Appl. No.: 14/386,364

(22) PCT Filed: Mar. 19, 2013

(86) PCT No.: PCT/JP2013/057779
§ 371 (c)(1),
(2) Date: Nov. 11, 2014

(87) PCT Pub. No.: WO2013/141229
PCT Pub. Date: Sep. 26, 2013

(65) Prior Publication Data
US 2015/0055090 A1 Feb. 26, 2015

(30) Foreign Application Priority Data
Mar. 21, 2012 (JP) ................................. 2012-064565

(51) Int. Cl.
*A61B 3/00* (2006.01)
*A61B 3/10* (2006.01)
(Continued)

(52) U.S. Cl.
CPC ............... *A61B 3/102* (2013.01); *A61B 3/0025* (2013.01); *A61B 3/1025* (2013.01); *A61B 3/14* (2013.01); *G02B 27/48* (2013.01)

(58) Field of Classification Search
CPC ..... A61B 3/102; A61B 3/0025; A61B 3/0075
See application file for complete search history.

(56) References Cited

U.S. PATENT DOCUMENTS

2007/0252951 A1   11/2007   Hammer et al.
2011/0007957 A1   1/2011    Sakagawa
(Continued)

FOREIGN PATENT DOCUMENTS

JP   2009-523564 A   6/2009
JP   2011-015850 A   1/2011
(Continued)

OTHER PUBLICATIONS

Yoshiaki Yasuno, "Modalities and properties of Fourier domain optical coherence tomography," Oyo Buturi, vol. 75, No. 6, 2006, pp. 707-712.

(Continued)

*Primary Examiner* — Jordan Schwartz
(74) *Attorney, Agent, or Firm* — Drinker Biddle & Reath LLP (57) ABSTRACT

Provided is a three-dimensional retina image generator that can detect, in a precise manner, the scanning position displacement during scanning of the retina with a simple configuration and, as a result, and can obtain a high-quality retinal image with a reduced influence of speckle noise therein. In order to detect the movement of retina R, the three-dimensional retina image generator has: second light source unit 210 that outputs a line beam to be imaged on retina R; positional displacement detector 220 that detects the line beam reflected from retina R and that detects the "displacement" of the scanning position during scanning of retina R; and dichroic mirror 230 that causes the line beam to propagate along the same light path as that of the object light scanning beam in inspection unit 140.

7 Claims, 7 Drawing Sheets

(51) Int. Cl.
*A61B 3/14* (2006.01)
*G02B 27/48* (2006.01)

(56) References Cited

U.S. PATENT DOCUMENTS

| | | | | |
|---|---|---|---|---|
| 2011/0116045 A1* | 5/2011 | Utagawa | ............... | A61B 3/102 351/210 |
| 2011/0286003 A1* | 11/2011 | Ono | ............... | A61B 3/102 356/495 |
| 2012/0147326 A1 | 6/2012 | Yatagai et al. | | |
| 2013/0195337 A1* | 8/2013 | Sakagawa | ............... | A61B 3/102 382/131 |

FOREIGN PATENT DOCUMENTS

| | | |
|---|---|---|
| JP | 2011-019576 A | 2/2011 |
| JP | 2011-212213 A | 10/2011 |
| JP | 2012-010960 A | 1/2012 |
| WO | WO-2006/105903 A2 | 10/2006 |
| WO | WO-2007/084750 A2 | 7/2007 |
| WO | WO-2010/083381 A1 | 7/2010 |
| WO | WO-2010/125394 A1 | 11/2010 |
| WO | WO-2011/007632 A1 | 1/2011 |
| WO | WO-2011/016437 A1 | 2/2011 |
| WO | WO-2012/002406 A1 | 1/2012 |

OTHER PUBLICATIONS

Curtis R. Vogel, et al., "Retinal motion estimation in adaptive optics scanning laser ophthalmoscopy," Optics Express, vol. 14, No. 2, Jan. 23, 2006, pp. 487-497.

Huang, D., et al., "Optical Coherence Tomography," Science, American Association for the Advancement of Science, U.S., vol. 254, No. 254, Nov. 22, 1991, pp. 1178-1181.

* cited by examiner

FIG. 7

THREE-DIMENSIONAL RETINA IMAGE GENERATOR

FIELD OF THE INVENTION

The present invention relates to a device for generating an image used in optical measurement of a retina.

BACKGROUND ART

In recent years, research has been advancing on optical tomographic image generating devices (hereinafter referred to as "OCT: Optical Coherence Tomographs") which visualize the depth structure of the inside of a biological body by making use of an interference effect of light.

In particular, recently, optical tomographic image generating devices for fundus oculi have emerged, in which three-dimensional images of the inside of a retina can be observed, and they have manifested their power in the diagnosis of illness with risks of vision loss.

Conventionally, in one of such optical tomographic image generating devices for fundus oculi, a low coherence interferometer has been used. As for such optical coherence eye-fundus tomography device, a time domain optical coherence eye-fundus tomography device (Time-Domain OCT, hereinafter referred to as "TD-OCT") is known, such device visualizing the depth structure of the inside of a biological body based on an interference signal in a depth direction of an object, which is obtained by mechanically manipulating a reference light path length.

Such TD-OCT has a low coherence light source with a wide wavelength width, and a light beam from such light source is divided into two beams and one of them is delivered to an object (i.e. an eye ball).

The TD-OCT causes the beam for scanning the object (hereinafter referred to as an "object-scanning light beam" or "probe light beam") to scan in a depth direction and to interfere with the beam for reference (hereinafter referred to as a "reference light beam"), which is the other of the divided beams. The TD-OCT then detects the position of diffusion in the object based on the interference fringes generated due to such interference.

Additionally, the TD-OCT causes the object-scanning light beam delivered to the object to scan in a direction lateral to a light path or causes the object to move in a direction lateral to such light path so that a cross sectional image of the object can be obtained (see, for example, Non-Patent Document 1).

On the other hand, a spectrum domain OCT (Fourier Domain OCT, hereinafter referred to as "FD-OCT") is known, such FD-OCT carrying out interference of light waves in a Fourier space (spectrum domain), instead of carrying out the same in the real space (time domain), without making use of such mechanical scanning in the depth direction. The FD-OCT has a measuring speed which is several tens of that of the TD-OCT.

In particular, the FD-OCT drives a galvanometer mirror to scan a retina forming plane and obtains a three-dimensional tomography image. Thus, since the FD-OCT can obtain a three-dimensional tomography image only with two-dimensional mechanical scanning, a rapid tomographic measurement can be performed (see, for example, Non-Patent Document 1).

On the other hand, in the FD-OCT, since no high-order aberration in a Zernike approximate polynomial is present, and by making use of a light beam only with low-order aberration (i.e. the object-scanning light beam), a component for correcting the high-order aberration is unnecessary, and thus, the number of components can be reduced. In addition, as to such FD-OCT, an FD-OCT which can maintain a high resolution for the images of a retina and a high operability of the device has emerged (see, for example, Patent Document 1).

Moreover, in an adaptively-controlled optics system (AO), a method is commonly known in which a movement distance of a retina is estimated by calculating mutual correlation between two images (see, for example, Non-Patent Document 2).

PRIOR ART REFERENCES

Patent Documents

Patent Document 1: WO2011/016437
Non-Patent Document 1: Yoshiaki Yasuno, "Fourier-Domain Optical Coherence Tomography," Applied Physics, Vol. 75, No. 6, pp. 707-712 (2006)
Non-Patent Document 2: Curtis R. Vogel, David W. Arathorn, Austin Roorda, Albert Parker, "Retinal Motion Estimation in Adaptive Optics Scanning Laser Ophthalmoscopy," Jan. 23, 2006, Vol. 14, No. 2, OPTICS EXPRESS

SUMMARY OF THE INVENTION

Problems to be Solved by the Invention

However, with the OCTs in the respective methods described above, since the retina constantly oscillates in a microscopic manner, in order to generate a precise three-dimensional image and to make an appropriate diagnosis, it is necessary to detect the movement of the retina in a precise manner. In particular, with the OCTs in the respective methods described above, it is difficult to detect the movement of the retina in a precise manner with an inexpensive configuration.

In addition, regarding the method for estimating the movement distance of the retina described above, no reference is made to the rapid formation of retinal images and neither is a device which embodies the same disclosed.

The present invention is made to solve the problems described above. An object of the present invention is to provide a device for generating a three-dimensional retinal image, which can detect, in a precise manner, the scanning position displacement during scanning of the retina with a simple configuration and, as a result, can obtain a high-quality retinal image with a reduced influence of speckle noise (random noise) therein.

Means for Solving the Problems (1) In order to solve the problems described above, a device for generating a three-dimensional retinal image according to the present invention has: a first light source unit that has a first light source; a light divider that divides an output light beam output from the first light source into an object-scanning light beam that is delivered to a retina of an eye ball and a reference light beam for reference; a reference light beam unit, into which the reference light beam is input and that causes the input reference light beam to reflect as a reference reflection light beam; a measurement unit that scans the retina by the object-scanning light beam and that causes light scattered at the retina to reflect as an object-reflected light beam; an interference intensity detector that generates an interference light beam in which the reference reflection light beam and the object-reflected light beam are caused to interfere with each other and that detects an interference intensity for each wavelength in the generated interference light beam; a generator that generates a three-dimensional image of the retina based on the detected interference intensity for each wavelength; a second light source unit that has a second light source for outputting a line beam and that outputs the line beam in order to transmit the line beam in a path identical to that of the object-scanning light beam in the measurement unit; and a positional displacement detector that has a line sensor, that detects the line beam reflected from the retina and output from the measurement unit by the line sensor and that detects scanning position displacement during scanning of the retina by the object-scanning light beam based on the detected line beam, wherein the measurement unit includes: a single light control mechanism that adjusts scanning positions when the line beam and the object-scanning light beam scan the retina; and a controller that performs control of the single light control mechanism, and wherein the controller controls the scanning positions when the line beam and the object-scanning light beam scan the retina in the single light control mechanism, based on the detected scanning position displacement.

By means of this configuration, the device for generating a three-dimensional retinal image of the present invention can cause the object-scanning light beam and the line beam to propagate so as to provide irradiation to the retina using one and the same light path in the measurement unit. More specifically, the device for generating a three-dimensional retinal image of the present invention can detect, in a precise manner, the scanning position displacement during scanning of the retina with a simple configuration, since it can make a light path of the beam for detecting the scanning position displacement during scanning of the retina identical with a light path of the beam for scanning the retina.

In addition, the device for generating a three-dimensional retinal image of the present invention can perform, when obtaining and averaging a plurality of face retinal images for one and the same position, alignment of the respective images, in a precise manner, since it can scan the retina while correcting the detected scanning position displacement during scanning of retina.

Accordingly, the device for generating a three-dimensional retinal image of the present invention can obtain a high-quality retinal image with a reduced influence of speckle noise (random noise) therein, such noise occurring due to the random interference between the object-scanning light beams.

(2) In addition, the device for generating a three-dimensional retinal image according to the present invention has the single light control mechanism that has a movable mirror, and the controls section that controls the movable mirror, based on the detected scanning position displacement, and that controls the scanning positions when the retina is scanned with the object-scanning light beam and the line beam.

By means of this configuration, the device for generating a three-dimensional retinal image of the present invention can detect the scanning position displacement during scanning of the retina and can perform, when obtaining and averaging a plurality of retinal images for one and the same position, alignment of the respective images, in a precise manner, with a simple configuration.

(3) In addition, the device for generating a three-dimensional retinal image according to the present invention has the positional displacement detector that generates an image of each line reflection beam, which is the reflected line beam, that calculates mutual correlation between two images obtained by the corresponding line reflection beams and that calculates the scanning position displacement during scanning of the retina based on the calculated mutual correlation.

By means of this configuration, the device for generating a three-dimensional retinal image of the present invention can detect, in a precise manner, the scanning position displacement during scanning of the retina by making use of a plurality of images which are obtained for positional displacement detection.

(4) In addition, the device for generating a three-dimensional retinal image according to the present invention has the positional displacement detector that divides each of the images obtained by the line reflection beams into a plurality of small regions with respect to the main scanning direction of a relevant line beam, that calculates the mutual correlation regarding two images of a small region that belongs to one and the same position in the main scanning direction in the two images, and that calculates the scanning position displacement during scanning of the retina based on the calculated mutual correlation.

By means of this configuration, the device for generating a three-dimensional retinal image of the present invention can perform the calculation of mutual correlation for detecting the scanning position displacement during scanning of the retina by two images of the small region that belongs to one and the same position in the main scanning direction, by making use of: two images that were created based on one line beam that serves as a reference such as the first scan lines, etc. when scanning the retina and one line beam of another scan line; two line beams having a relationship of a certain interval therebetween; or line beams in two neighboring scan lines.

Accordingly, the device for generating a three-dimensional retinal image of the present invention can detect the scanning position displacement during scanning of the retina in a prompt manner, as long as images of a relevant small region can be obtained, as compared to the case in which the images produced by the line beam are obtained for each of the entire two scan line.

Consequently, the device for generating a three-dimensional retinal image of the present invention can detect, in a precise and prompt manner, the scanning position displacement during scanning of the retina by making use of a plurality of images obtained for positional displacement detection.

(5) In addition, the device for generating a three-dimensional retinal image according to the present invention has the positional displacement detector that calculates the mutual correlation of the overlapping image region with regard to two images of small regions that belong to one and the same position in the main scanning direction of two line reflection beams, the scan lines of the line reflection beams in the main scanning direction being located next to each other.

By means of this configuration, the device for generating a three-dimensional retinal image of the present invention can detect the scanning position displacement during scanning in a prompt and precise manner, since it can detect the scanning position displacement during scanning of the retina by making use of neighboring scan lines.

(6) In addition, the device for generating a three-dimensional retinal image according to the present invention has the line beam that is a beam that extends in the sub-scanning direction of the object-scanning light beam.

By means of this configuration, the device for generating a three-dimensional retinal image of the present invention can detect the scanning position displacement in a precise manner, since it can secure a predetermined size for an image to be used when detecting the scanning position displacement.

Effect of the Invention

The device for generating a three-dimensional retinal image according to the present invention can detect the scanning position displacement during scanning of the retina, in a precise manner, with a simple configuration, since it can make a light path of the beam for detecting scanning position displacement during scanning of the retina identical with a light path of the beam for scanning the retina.

In addition, the device for generating a three-dimensional retinal image according to the present invention can obtain an image having image distortion arising from the scanning position displacement removed therefrom and also can perform, when obtaining and averaging a plurality of retinal OCT images for one and the same position, alignment of the respective images, in a precise manner, since it can scan the retina while correcting the detected scanning position displacement.

Accordingly, the device for generating a three-dimensional retinal image of the present invention can obtain a high-quality retinal OCT image with a reduced influence of speckle noise (random noise) therein, such noise occurring due to the random interference between the object-scanning light beams.

EMBODIMENTS OF THE INVENTION

The embodiments described hereinafter are optical tomographic image generating devices for fundus oculi, which make use of an adaptively-controlled optics system (AO) and which are applied with a device for generating a three-dimensional retinal image. The details of the following embodiments will be described with reference to the drawings.

[Optical Coherence Eye-Fundus Tomography Device]

First, a configuration of an embodiment of optical coherence eye-fundus tomography device 100 will be described using FIGS. 1 and 2.

Figure 1:
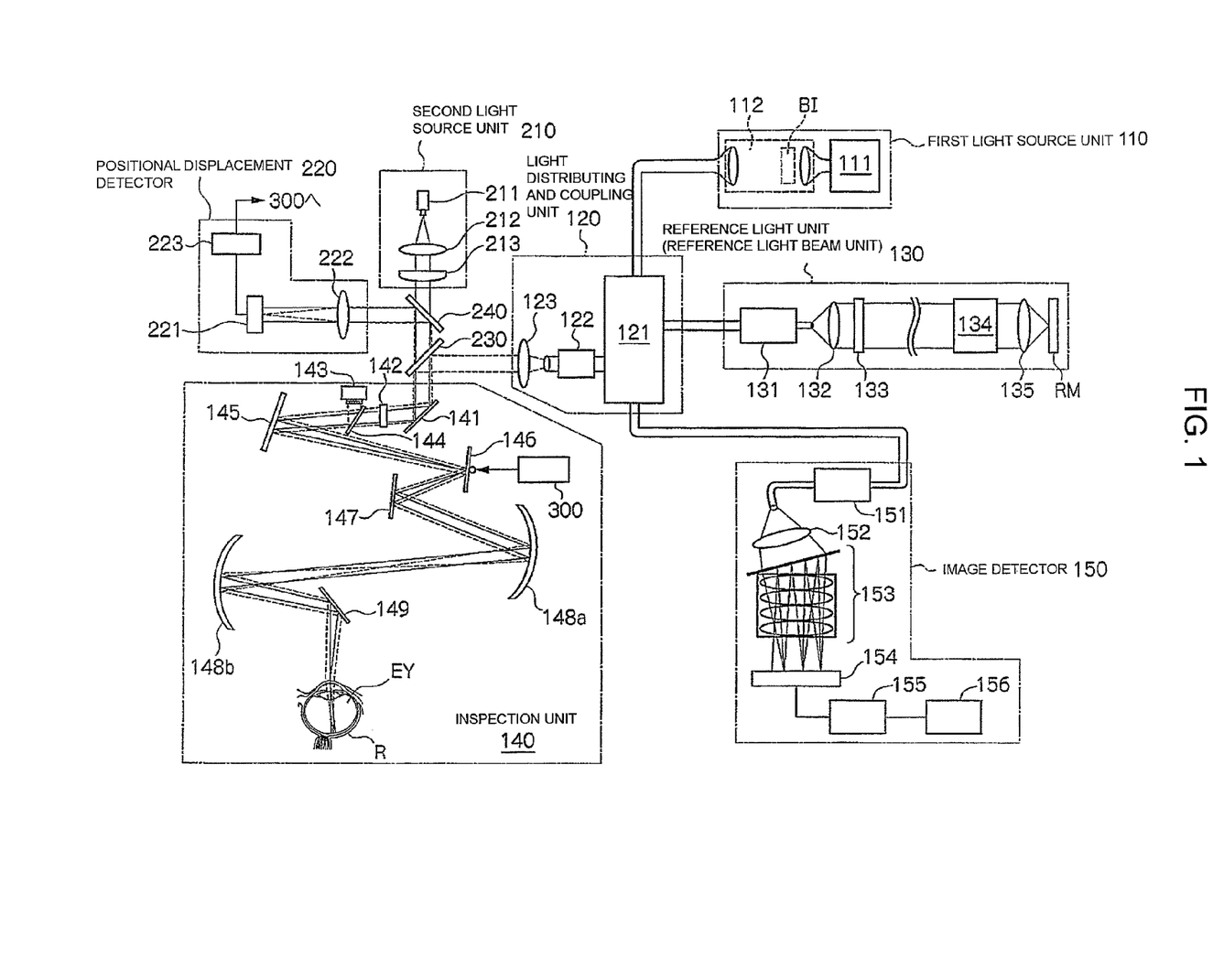
FIG. 1 is a block diagram illustrating a configuration of an embodiment of an optical coherence eye-fundus tomography device according to the present invention.
Figure 2:
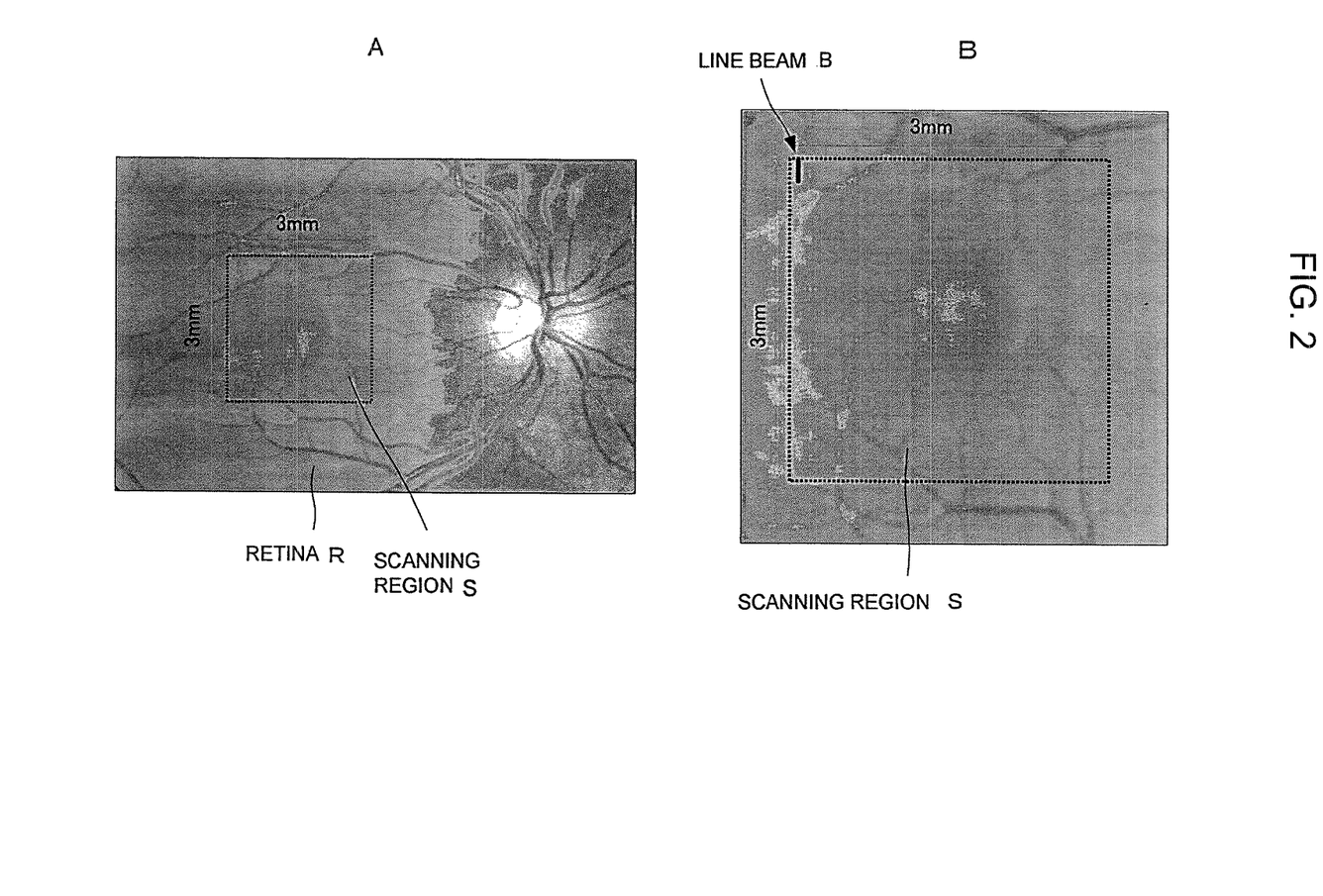
FIG. 2 contains diagrams for describing a scanning region of a retina in an embodiment.
Figure 3:
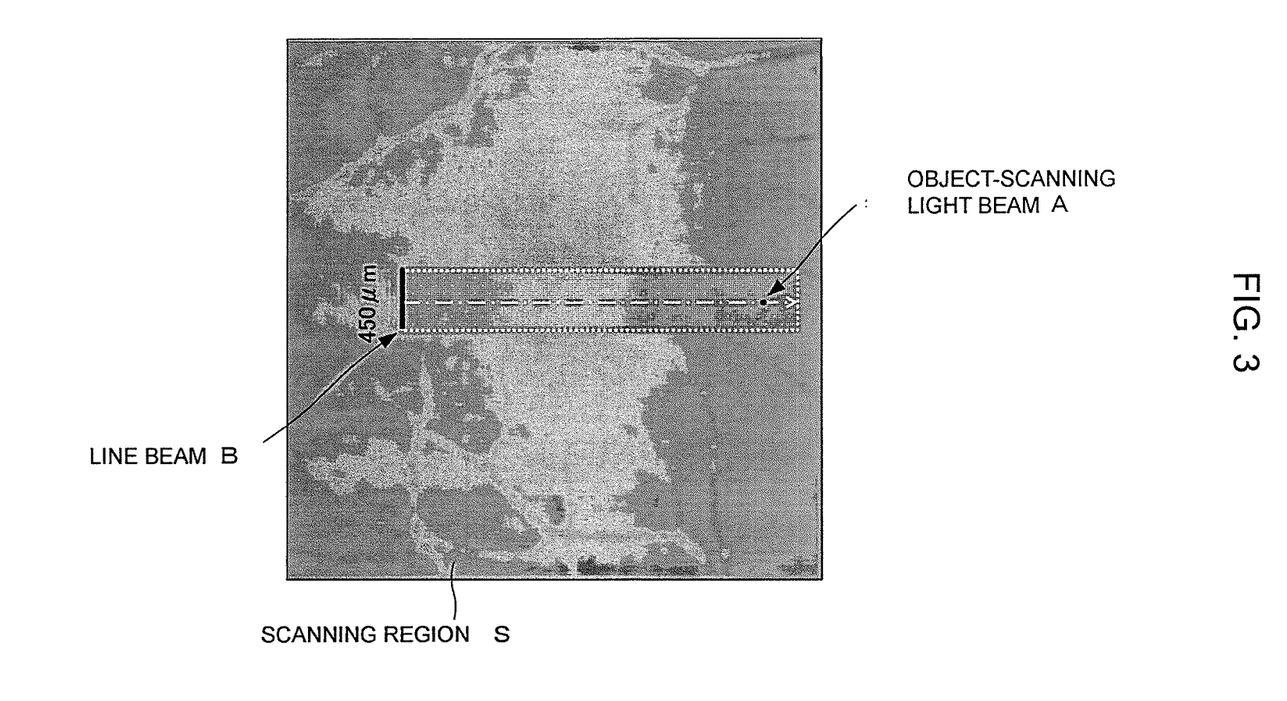
FIG. 3 is a diagram for describing the relationship between an object-scanning light beam and a line beam, which are delivered to a retina, in an embodiment.
Figure 4:
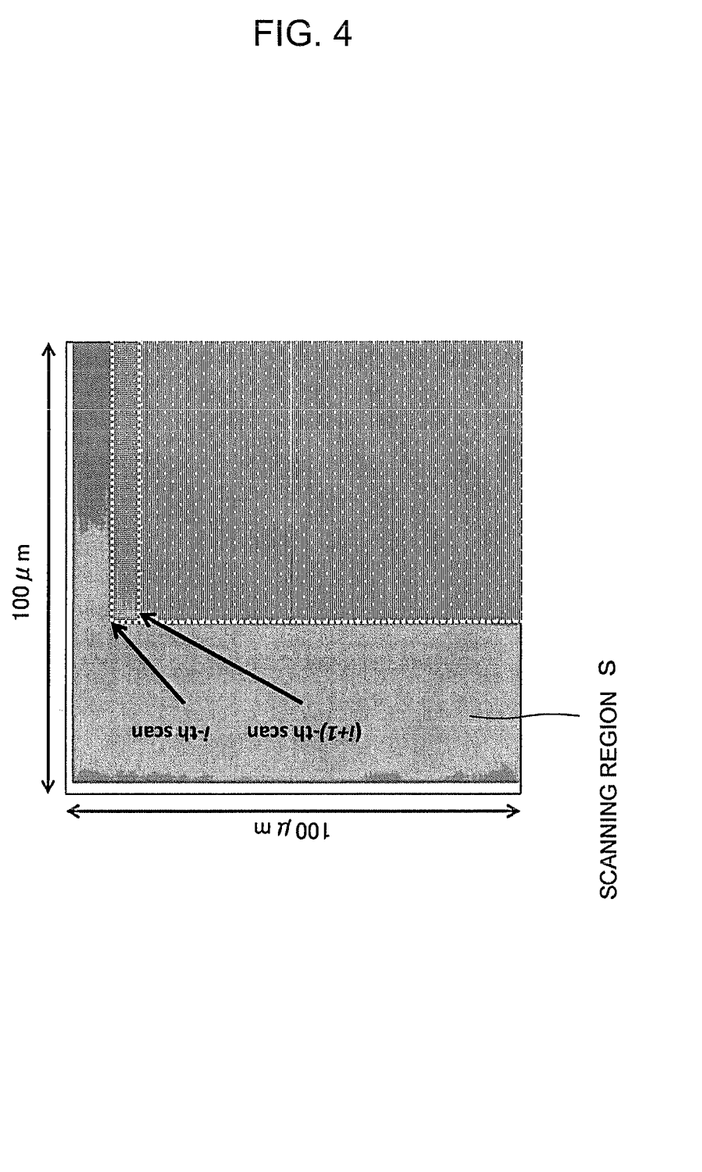
FIG. 4 is a diagram for describing the scanning of a line beam on a retina in an embodiment.

FIG. 1 is a block diagram illustrating the configuration of optical coherence eye-fundus tomography device 100 in the present embodiment. FIG. 2(A) is a diagram for describing scanning region S in retina R and FIG. 2(B) is an enlarged view of FIG. 2(A). Furthermore, FIG. 3 is a diagram for describing the relationship between an object-scanning light beam and a line beam, which are delivered to retina R and FIG. 4 is a diagram for describing the scanning of a line beam on retina R.

Optical coherence eye-fundus tomography device 100 of the present embodiment is an OCT-measuring device which makes use of an adaptively-controlled optics system (AO) technique and obtains a tomographic image of an object, which is an inspection target (i.e. eyeball EY and, in particular, retina R, in the present embodiment) using a light interference effect.

Optical coherence eye-fundus tomography device 100 divides a light source beam (hereinafter also referred to as an "outgoing light beam") into an object-scanning light beam (hereinafter referred to as an "object-scanning light beam") to be delivered to the inspection target and a reference light beam which serves as a reference when performing an interference measurement. Optical coherence eye-fundus tomography device 100 causes an object-reflected light beam, which is the object-scanning light beam delivered to the object and reflected therefrom, and a reference reflection light beam, which is the reference light beam reflected from a predetermined reflection mirror RM, to interfere with each other.

Optical coherence eye-fundus tomography device 100 scans retina R by the object-scanning light beam in a first direction (width direction), which is substantially parallel to a retina forming plane in which retina R is formed, and in a second direction (longitudinal direction), which is substantially parallel to the retina forming plane and is substantially perpendicular to the first direction.

Optical coherence eye-fundus tomography device 100 then generates a tomographic image of retina R including a depth direction of retina R, which is parallel to a travelling direction (optical axis direction) of the object-scanning light beam, based on the object-reflected light beam and the reference reflection light beam which are made to interfere with each other for every point (hereinafter also referred to as a "scanning position" or "irradiation position").

In particular, as shown in FIG. 1, optical coherence eye-fundus tomography device 100 of the present embodiment has: first light source unit 110 that delivers a light source beam; and light distributing and coupling unit 120 that distributes the delivered light source beam into a reference light beam and an object-scanning light beam and that causes a reference reflection light beam and an object-reflected light beam to interfere with each other.

Optical coherence eye-fundus tomography device 100 is configured from: reference light unit 130 that causes the reference light beam to be reflected and that causes the reference reflection light beam, which is the reflected reference light beam, to enter light distributing and coupling unit 120; inspection unit 140 that causes the object-scanning light beam to be delivered on retina R and that causes the object-reflected light beam to enter light distributing and coupling unit 120: and image detector 150 that obtains a tomographic image of the object based on a light beam (hereinafter referred to as an "interference light beam") in which the object-reflected light beam and the reference reflection light beam are made to interfere with each other.

Furthermore, optical coherence eye-fundus tomography device 100 has: second light source unit 210 that outputs a light beam to be imaged on retina R in line form (hereinafter referred to as a "line beam") in order to detect the movement of eye ball EY, namely, the movement of retina R; positional displacement detector 220 that detects the line beam reflected from retina R (hereinafter referred to as a "line reflection beam") and that detects the "displacement" of the scanning position during scanning of retina R; dichroic mirror 230 that causes the line beam to propagate along the same light path as that of the object light scanning beam in inspection unit 140: and beam splitter 240 that outputs the line reflection beam output from inspection unit 140 to positional displacement detector 220.

For example, first light source unit 110 of the present embodiment configures a first light source unit of the present invention and light distributing and coupling unit 120 serves as a light splitter. In addition, for example, reference light unit 130 of the present embodiment serves as a reference light beam unit of the present invention and inspection unit 140 serves as a measurement unit of the present invention. Furthermore, for example, image detector 150 of the present embodiment serves as an interference intensity detector and a generator of the present invention, and second light source unit 210 serves as a second light source unit of the present invention. Moreover, for example, positional displacement detector 220 of the present embodiment serves as a positional displacement detector of the present invention.

First light source unit 110 outputs light which is temporally incoherent and is spatially coherent.

For example, first light source unit 110 of the present embodiment is provided with: first irradiation light source 111 that delivers a light source beam; and calibration part 112 that has light isolator BI and that performs a predetermined calibration using glass with respect to the light source beam delivered from first irradiation light source 111.

First irradiation light source 111 is configured by a super luminescent diode and, specifically, it delivers a light beam having a wavelength in the ranges of 780 nm-920 nm and 1000 nm-1100 nm, as the light source beam.

It should be note that, in the present embodiment, a light source beam having a wavelength of 780 nm is used. However, the light source beam is not limited to the above wavelength and any light source beam that is not bright to the eyes and that has a certain illuminance at a point light source will also be sufficient.

Calibration part 112 transmits a light beam delivered from first irradiation light source 111 only to light distributing and coupling unit 120. Further, calibration part 112 has light isolator BI that does not transmit the light beam in the opposite direction in which the light beam is transmitted, and performs a predetermined calibration with respect to the light source beam.

Light distributing and coupling unit 120 has: light distributor/coupler 121; second polarization controller 122 that controls the polarization of the divided object-scanning light beam and the reflected object-reflected light beam; and conversion lens 123, for the light distributing and coupling unit, that converts the divided object-scanning light beam into a parallel light beam and the object-reflected light beam into a condensed light beam.

Light distributor/coupler 121 divides the input light source beam into an object-scanning light beam and a reference light beam by an optical fiber, a beam splitting prism, or the like. The light beams are respectively output to inspection unit 140 and reference light unit 130.

For example, light distributor/coupler 121 of the present embodiment has a predetermined distribution ratio (for example, a distribution ratio of approximately 50:50 to approximately 80:20). The input light source beam is divided based on such distribution ratio and an output is made to each of inspection unit 140 and reference light unit 130.

In addition, the object-reflected light beam which is reflected from the object in inspection unit 140 and the reference reflection light beam which is reflected in reference light unit 130 are made to enter light distributor/coupler 121.

Such light distributor/coupler 121 then causes the input object-reflected light beam and reference reflection light beam to interfere with each other and outputs the resultant inference light beam to image detector 150.

For example, light distributor/coupler 121 of the present embodiment has a predetermined coupling ratio (for example, the coupling ratio of approximately 50:50 to approximately 80:20), causes the input object-reflected light beam and reference reflection light beam to couple and to interfere with each other based on such coupling ratio, and causes the resultant coupled and interfered interference light beam to be output to image detector 150.

Second polarization controller 122 causes each of the input object-scanning light beam and reference light beam to be polarized so as to prevent interference therebetween.

Conversion lens 123 for the light distributing and coupling unit is formed by a collimator lens and converts the object-scanning light beam output from light distributor/coupler 121 into a parallel light beam and outputs such parallel light beam to dichroic mirror 230.

Reference light unit 130 is basically a unit for generating a reference reflection light beam which serves as a reference in a light path having the same length as that of the light path of the object-scanning light (reflection light) beam. However, in reality, the light path in the reference light unit has a slight light path difference ($\tau$) based on the depth necessary for the diagnosis in the light source beam from the light path of the object-scanning light (reflection light) beam.

Specifically, reference light unit 130 of the present embodiment has: first polarization controller 131 that controls the polarization of the divided object-scanning light beam and the reflected reference reflection light beam; first conversion lens 132 that converts the reference light beam into a parallel light beam and condenses the reference reflection light beam which is a parallel light beam: and achromatic lens 133 that performs correction of chromatic aberration.

Reference light unit 130 also has: water vial 134 that adjusts chromatic dispersion; reflection mirror RM that causes the reference light beam to reflect therefrom; and second conversion lens 135 that condenses the reference light beam which is a parallel light beam and that converts the condensed reference reflection light beam into a parallel light beam.

In particular, achromatic lens 133 and water vial 134 are provided in order to create a pseudo-environment identical to an environment in which the object-scanning light beam (in particular, object-reflected light beam) is transmitted through the eye ball in inspection unit 140.

Usually, the achromatic lens and water vial 134 correct chromatic aberration or chromatic dispersion that occurs when eye ball EY is irradiated with light beams; however, in reference light unit 130, they generate a light beam, in a pseudo-manner, in which chromatic aberration or chromatic dispersion is performed in inspection unit 140.

First polarization controller 131 causes each of the reflected reference reflection light beam and the reference light beam to be polarized so as to prevent interference therebetween.

Second light source unit 210 is provided with: second irradiation light source 211 that delivers a light source beam; conversion lens 212 for the second light source unit that converts the light source beam delivered from second irradiation light source 211 into a parallel light beam; and cylindrical lens 213 that converts the parallel light beam into a line beam.

It should be noted that, for example, second irradiation light source 211 serves as a second light source of the present invention.

Second irradiation light source 211 is configured by a super luminescent diode and, specifically, it delivers a light beam having a wavelength different from that of first irradiation light source 111, as a light source beam. In addition, for example, second irradiation light source 211 of the present embodiment delivers a light beam having a wavelength of 700 nm or 900 nm, as a light source.

It should be noted that second irradiation light source 211 delivers not only the light source beam having the above wavelength but also any light source beam that has a wavelength different from that of first radiation light source 111 and that is not bright to the eyes and that has a certain illuminance at a point light source will also be sufficient.

Conversion lens 212 for the second light source unit is formed by a collimator lens and converts the light source beam delivered from second irradiation light source 211 into a parallel light beam and outputs such parallel light beam to cylindrical lens 213.

Cylindrical lens 213 converts and outputs the parallel light beam into a line beam to be imaged on retina R in line form. Namely, cylindrical lens 213 outputs a line beam that extends over retina R in a longitudinal direction which is a vertical direction ( ) at the time of inspection and which is a longitudinal direction in the plane of paper of FIG. 2(B)), and serves as the object-scanning light beam.

For example, in the present embodiment, cylindrical lens 213 converts and outputs a light beam having a width of 450 μm (in the longitudinal direction of retina R) and a thickness of 13 μm (in the width direction of retina R. Namely, the lateral direction in the plane of paper of FIG. 2(B)) into a line beam that can be delivered onto retina R via scanning mirror 146, which will be described later.

It should be noted that the scanning in the width direction of retina R, i.e. the scan line direction, is referred to as "main scanning" and the movement to the next scan line, i.e. the movement of the line beam in the longitudinal direction of retina R is referred to as "sub-scanning."

Beam splitter 240 is provided on the light path of the line beam output from cylindrical lens 213. Beam splitter 240 transmits and outputs the line beam output from cylindrical lens 213 to inspection unit 140 and causes a line reflection beam output from inspection unit 140 to be reflected to positional displacement detector 220 which is provided in a direction orthogonal to the light path of the line beam.

For example, beam splitter 240 has transmittance and reflectance that allows 90% of the line beam output from cylindrical lens 213 to be transmitted therethrough and 10% thereof to be reflected therefrom, and allows 90% of the line reflection beam to be reflected therefrom and 10% thereof to be transmitted therethrough.

Dichroic mirror 230 is provided on the light path of the line beam output from cylindrical lens 213 via beam splitter 240.

Dichroic mirror 230 transmits and outputs the line beam output from cylindrical lens 213 via beam splitter 240 to inspection unit 140, and reflects and outputs the object-scanning light beam output from the direction orthogonal to the light path of the line beam output from cylindrical lens 213 to inspection unit 140.

On the other hand, dichroic mirror 230 reflects and outputs the object-reflected light beam that is reflected from retina R in a direction orthogonal to the light path of the line beam, and causes such object-reflected light beam to enter light distributing and coupling unit 120. Dichroic mirror 230 then transmits therethrough the line reflection beam that is reflected from retina R and causes the same to enter positional displacement detector 220 via beam splitter 240.

Namely, dichroic mirror 230 is arranged and configured such that a light beam having a different wavelength is caused to be transmitted therethrough or reflected therefrom so as to cause the line beam to propagate along the same light path as that of the object scanning line beam in inspection unit 140 and to cause the respective light beams output from inspection unit 140 to be able to output to a corresponding light path.

In order to detect scanning position displacement during scanning of retina R, inspection unit 140 adjusts the irradiation position of the line beam on retina R and performs scanning of retina R by the object-scanning light beam while correcting the position of such scanning, based on the detected scanning position displacement.

In particular, as described above, inspection unit 140 is configured, when scanning along two axes, i.e. in one direction in retina R (for example, the width direction of retina R) and in the other direction (for example, the longitudinal direction of retina R) orthogonal to such one direction by the object-scanning light beam, such that retina R is irradiated, during one scanning of the object-scanning light beam, with the line beam having the line scanned by such one scanning located in the middle, as shown in FIG. 3.

Specifically, inspection unit 140 of the present embodiment is configured from: first planar mirror 141; achromatic lens 142; wavefront sensor 143 that detects wavefront aberration of the object-reflected light beam; prism 144 for the sensor that divides the object-reflected light beam and causes part thereof to enter wavefront sensor 143; deformable mirror 145; scanning mirror 146; second planar mirror 147; pair of concave mirrors 148; third planar mirror 149; and controller 300 that controls scanning mirror 146 to controlling the irradiation position of the light beam on retina R.

For example, the scanning mirror of the present embodiment serves as a light control mechanism and a movable mirror of the present invention. Further, achromatic lens 142 may be omitted from such configuration.

First planar mirror 141, second planar mirror 147 and third planar mirror 149 are used for forming light paths (hereinafter referred to as "light paths within the inspection unit") along which the object-scanning light beam, the object-reflected light beam, the line beam and the line reflection light beam are propagated, in order to miniaturize inspection unit 140 and to arrange other members at appropriate positions.

Wavefront sensor 143 of the present embodiment is configured by a Shack-Hartmann sensor and detects the wavefront aberration of the object-reflected light beam that is reflected from retina R.

The shape of the mirror surface of deformable mirror 145 is controlled by wavefront sensor 143, and deformable mirror 145 reflects each of the object-scanning light beam which is transmitted through achromatic lens 142 and the object-reflected light beam which is reflected from retina R to a corresponding direction. In addition, under the predetermined control, the mirror surface structure of deformable mirror 145 changes based on the wavefront aberration of the object-reflected light beam which is detected by wavefront sensor 143.

Scanning mirror 146 is a single light control mechanism (i.e. a single movable mirror) used for simultaneously controlling the scanning positions on retina R of the object-scanning light beam and the line beam. In particular, scanning mirror 146, under the control of controller 300, is formed so as to perform, while reflecting the object-scanning light beam and the line beam, the scanning in the width direction of retina R with respect to the retina forming plane in which retina R is formed, and the scanning in the longitudinal direction which is substantially parallel to the retina forming plane and which is orthogonal to the width direction of retina R.

Specifically, when scanning along two axes, i.e. in the width direction and in the longitudinal direction which is orthogonal to such width direction in retina R, by the object-scanning light beam and the line beam, scanning mirror 146, while interlocking the object-scanning light beam and the line beam with each other, moves the imaging line of the line beam on retina R and the imaging point of the object-scanning light beam on retina R from right to left and up and down.

For example, scanning mirror 146 of the present embodiment is made such that the oscillation angles in both the vertical and horizontal directions are 0.3 degrees and such that the scanning position on the retina can move over a distance of 100 μm. When the inspection region (i.e. scanning region S in the object-scanning light beam) in retina R shown in FIGS. 2(A) and 2(B) has a size of 3 mm×3 mm, the scanning angles (oscillation angles) of scanning mirror 146 can be adjusted up to a maximum of 10 degrees in both the vertical and horizontal directions, and scanning mirror 146 images the object-scanning light beam and line beam B onto the scanning positions on retina R.

In addition, as shown in FIG. 3, scanning mirror 146 controls the irradiation directions of object-scanning light beam A and line beam B on retina R such that retina R is scanned in the width direction thereof, while object-scanning light beam A is imaged onto the middle (i.e. the middle in the longitudinal length) of line beam B having a predetermined length (for example, 450 μm) in the longitudinal direction of retina R.

Then, when one scanning in the width direction is completed, scanning mirror 146 controls the irradiation directions of object-scanning light beam A and line beam B such that the object-scanning light beam moves, in the longitudinal direction, to the next scan line so as to restart the scanning in the width direction and, as shown in FIG. 4, such that the line beam also moves to the next scan line.

It should be noted that FIG. 4 shows a condition in which, in scanning region S, retina R is scanned along scan lines by the object-scanning light beam every 6 μm and, more specifically, a condition in which retina R is irradiated with an $i^{th}$ line beam and an i+$1^{th}$ line beam.

In addition, during scanning when retina R is scanned by the object-scanning light beam, scanning mirror 146 corrects the position on retina R to be scanned by the object-scanning light beam and the light beam, based on the amount of the scanning position displacement during scanning of retina R, which is detected by positional displacement detector 220.

Namely, as shown in FIGS. 3 and 4, when scanning retina R by object-scanning light beam A and line beam B, scanning mirror 146 is used to control, in real time, the position on retina R to be scanned by object-scanning light beam A, i.e. the imaging position of object-scanning light beam A on retina R.

Pair of concave mirrors 148 is used for making the object-scanning light beam and the line beam which are reflected by scanning mirror 146 enter eye ball EY and image such object-scanning light beam and the line beam onto retina R.

It should be noted that the object-reflected light beam and the line reflection beam which are reflected from retina R travel along a path reverse to that described above (i.e. the return path) and are output from inspection unit 140. The object-reflected light beam then enters image detector 150 via dichroic mirror 230 and light distributing and coupling unit 120. The line reflection beam enters positional displacement detector 220 via dichroic mirror 230 and beam splitter 240.

Controller 300 controls the irradiation directions of the object-scanning light beam and the line beam by scanning mirror 146, based on the instructions from positional displacement detector 220. More specifically, controller 300 controls the scanning position during scanning of retina R by object-scanning light beam by controlling scanning mirror 146, based on the detected amount of the scanning position displacement during scanning of retina R by the object-scanning light beam.

Specifically, controller 300 controls the moving of scanning mirror 146 and, as described above, controls the scanning positions of the line beam, and object scanning light beam on retina R. More specifically, controller 300 controls, regarding the line beam and the object-scanning light beam, the scanning in the width direction of retina R with respect to the retina forming plane and the scanning in the longitudinal direction which is substantially parallel to the retina forming plane and which is orthogonal to the width direction of retina R.

It should be noted that, in the region on retina R having a size of 3 mm×3 mm shown in FIG. 3, as will be described later, when a scan line interval is assumed to be 6 μm, controller 300 performs movement (i.e. scanning) of object-scanning light beam A and line beam B in the width direction of retina R 500 times, while interlocking object-scanning light beam A and line beam B with each other and moving along the scan lines in the longitudinal direction of retina R.

Image detector 150 extracts each wavelength from the interference light beam and calculates the interference intensity in each wavelength for every scanning position (each point to be scanned in the width direction and the longitudinal direction of the retina forming plane), and calculates and displays light intensity data in the depth direction (data indicating the reflection distribution coefficients in the depth direction) based on the calculated interference intensity of each wavelength.

Usually, depending on the point where the object-scanning light beam reflected in retina R, the difference in distance for the light path from the reference reflection light beam changes and, consequently, the interference intensity changes with each wavelength.

Accordingly, image detector 150 of the present embodiment detects such changed interference intensities and transforms such interference intensities, which are wavelength domain data, into spatial domain data through a Fourier transformation, and can calculate the light intensity data in the depth direction in retina R.

Specifically, the interference light beam, in which the object-reflected light beam transmitted from inspection unit 140 and the reference reflection light beam transmitted from reference light unit 130 are coupled and made to interfere with each other, is input into image detector 150 of the present embodiment.

In addition, image detector 150 is provided with: third polarization controller 151 that controls the polarization of the interference light beam; conversion lens 152 for the image detector that converts the polarized interference light beam into a parallel light beam; and grating part 153 that disperses the interference light beam, which is a parallel light beam, for each wavelength.

Further, image detector 150 is provided with: scanning camera 154 that detects the interference intensity for each wavelength; image generation part 155 that performs three-dimensionalization of retina R by calculating the light intensity data based on the detected interference intensity for each wavelength; and display part 156 that displays the three-dimensionally imaged image data.

In particular, image generation part 155 can obtain a retinal image with a reduced influence of speckle noise (random noise) therein by producing a plurality of retinal images for one and the same position based on the light intensity data and by adding and averaging such images, while aligning the respective images.

Positional displacement detector 220 is provided with: line sensor 221; conversion lens 222 for the positional displacement detector for condensing the line reflection beam output from beam splitter 240 to line sensor 221; and positional displacement detector 223. For example, line sensor 221 of the present embodiment serves as a line sensor of the present invention.

Line sensor 221 is a line scan camera having CCD elements which outputs information on the intensity of the line reflection beam received by each of the CCD elements. It should be noted that the line scan camera may be a color camera or a black-and-white camera.

Conversion lens 212 for the line sensor is formed by a collimator lens and condenses the line reflection beam output from beam splitter 240 to line sensor 221.

Positional displacement detector 223 calculates the amount of movement of retina R, i.e. the amount of the scanning position displacement during scanning, based on the line reflection beam detected by line sensor 221, and outputs instructions to controller 300 for controlling the irradiation direction of the object-scanning light beam in scanning mirror 146, based on the calculated result.

More specifically, positional displacement detector 223 generates an image from the line reflection beam, divides such generated image into a predetermined number in the scan line direction, and detects the amount of the scanning position displacement during scanning of retina R, based on the images of a small region for one and the same position of two neighboring scan lines.

For example, positional displacement detector 223 of the present embodiment divides the generated image into 12 parts in the scan line direction, and detects the amount of the scanning position displacement during scanning of retina R, based on the images of a small region for one and the same position of two neighboring scan lines.

The principle of detecting positional displacement by positional displacement detector 223 of the present embodiment will be described later.

[Method for Calculating Light Intensity Data]

Figure 5:
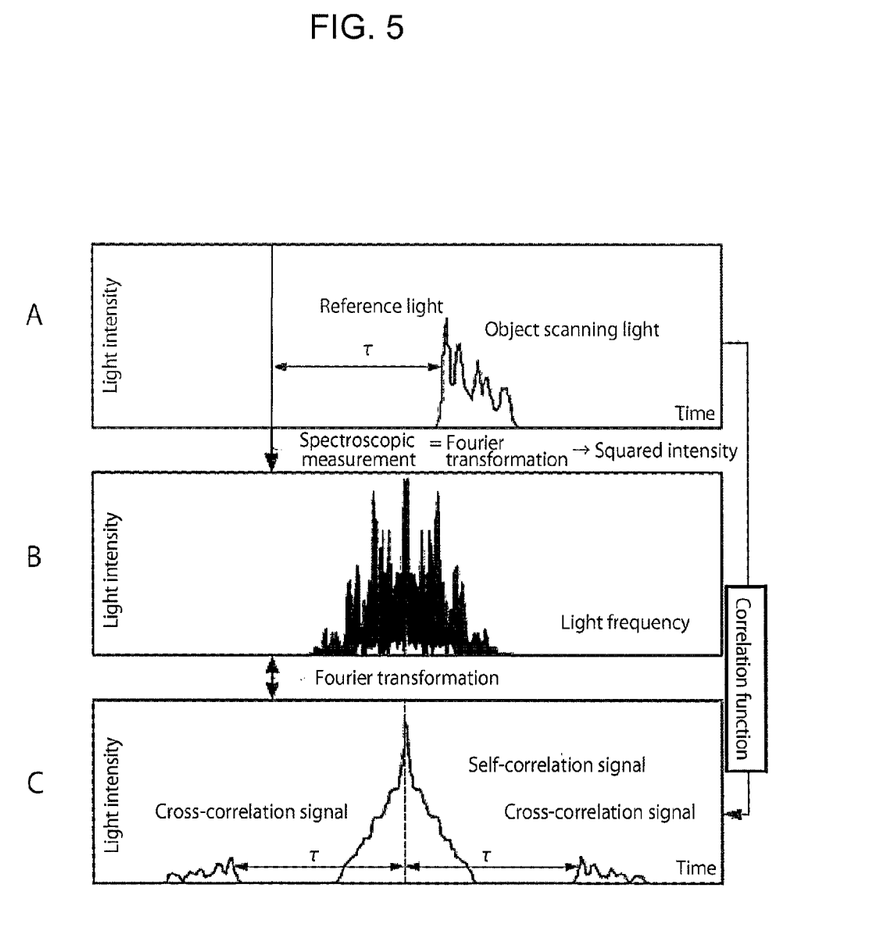
FIG. 5 contains diagrams for describing a method for calculating the interference intensities in a reference reflection light beam and an object-reflected light beam.

Subsequently, a method for calculating light intensity data in the depth direction of retina R from the interference intensity data for each wavelength will be described, using FIG. 5. FIG. 5 contains diagrams for describing a method for calculating the interference intensities in a reference reflection light beam and an object-reflected light beam.

Assuming that the depth direction of an object, i.e. the optical axis direction of a light beam is a z axis, a light object-scanning light beam (Ep(t)) can be expressed as formula 1 below by denoting the characteristics of reflection and scattering by the structure of retina R as (s(z) and the light beam delivered from light source 110 as (E(t)).

$$Ep(t)=E(t) \otimes s(t) \qquad \text{[Formula 1]}$$

It should be noted that the symbol with a cross mark in a circle denotes convolution. In addition, the reason why formula 1 is expressed by a function of time is because the propagation directions of the z axis and the light beam are the same and the propagation distance is converted into time, and thus, (s(z)) is expressed by a function of time (s(t)).

Further, reference light unit 130 and inspection unit 140 are given a light path difference (τ) in advance, and light amplification signals of the reference reflection light beam and the object-reflected light beam which enter light distributing and coupling unit 120 become as shown in FIG. 5(a).

The light interference intensities, i.e. the spectrum interference fringes (E(ω)=F[Ep(t)]), of the reference reflection light beam and the object-reflected light beam, which are dispersed and have undergone a Fourier transformation by grating part 153, are then detected by scanning camera 154 (see FIG. 5(b)).

At this point, the relationship between Fourier interference signal F[I], which is obtained by applying a Fourier transformation to interference signal I, and the spectrum interference fringes is indicated in formula 2 below, where E* denotes a complex conjugation.

$$F[I(\omega)] = |F[Ep(\omega)] + F[Ep(\omega)]|^2 \qquad \text{[Formula 2]}$$
$$= |F[Ep(\omega)]|^2 + |F[Ep(\omega)]|^2 + F[Ep(\omega)]$$
$$F[Er^*(\omega)] + F[Ep^*(\omega)]F[Er(\omega)]$$

In addition, this formula 2 can be expressed by formula 3, based on a correlation operation (*).

$$F[I(\omega)]=Ep(t)*Ep^*(t)+Ep(t)*Er^*(t)+Ep(t)*Ep^*(t)+Ep(t)*Er^*(t) \qquad \text{[Formula 3]}$$

Here, the first and second terms on the right side respectively denote autocorrelation signals of the reference reflection light beam and the object-reflected light beam and correspond to the peak in the center of FIG. 5(c). The third and fourth terms on the right side respectively denote mutual correlation of the reference reflection light beam and the object-reflected light beam and they appear at positions spaced apart from the autocorrelation signals in a symmetrical manner.

In addition, the third term ($I_{third\ term}$) on the right side becomes formula 4 below, based on the relationship of formula 1; however, since the reference light beam becomes the reference reflection light beam by being reflected from a planar mirror and since {Er(t)=E(t)}, the third term will be a convolution of an autocorrelation function of the light source (light source beam) and the optical axis direction (the so-called depth direction).

$$I_{third\ term}=(Er(t)*E(t)) \otimes s(t) \qquad \text{[Formula 4]}$$

More specifically, when the pulse width of the light source beam is sufficiently short or when the spectrum distribution is sufficiently broad, E(t) can be considered as a delta function and thus, since the intensities of these mutual correlation signals correspond to the reflection and scattering characteristics in the depth direction of the object, the data on the depth direction can be obtained by the data on the interference intensity, without the need to scan in the depth direction in the spectrum domain.

It should be noted that the resolution in the depth direction (Δz) can be expressed as formula 5 below, using central wavelength λ and wavelength width Δλ of the light source beam, where σ denotes a wavelength spreading width of a Gaussian distribution.

$$\Delta z = 2\sqrt{2\ln 2\sigma} = \frac{2\ln 2}{\pi} \frac{\lambda^2}{\Delta\lambda} \qquad \text{[Formula 5]}$$

[Positional Displacement Detection Principle and Positional Displacement Detector]

Figure 6:
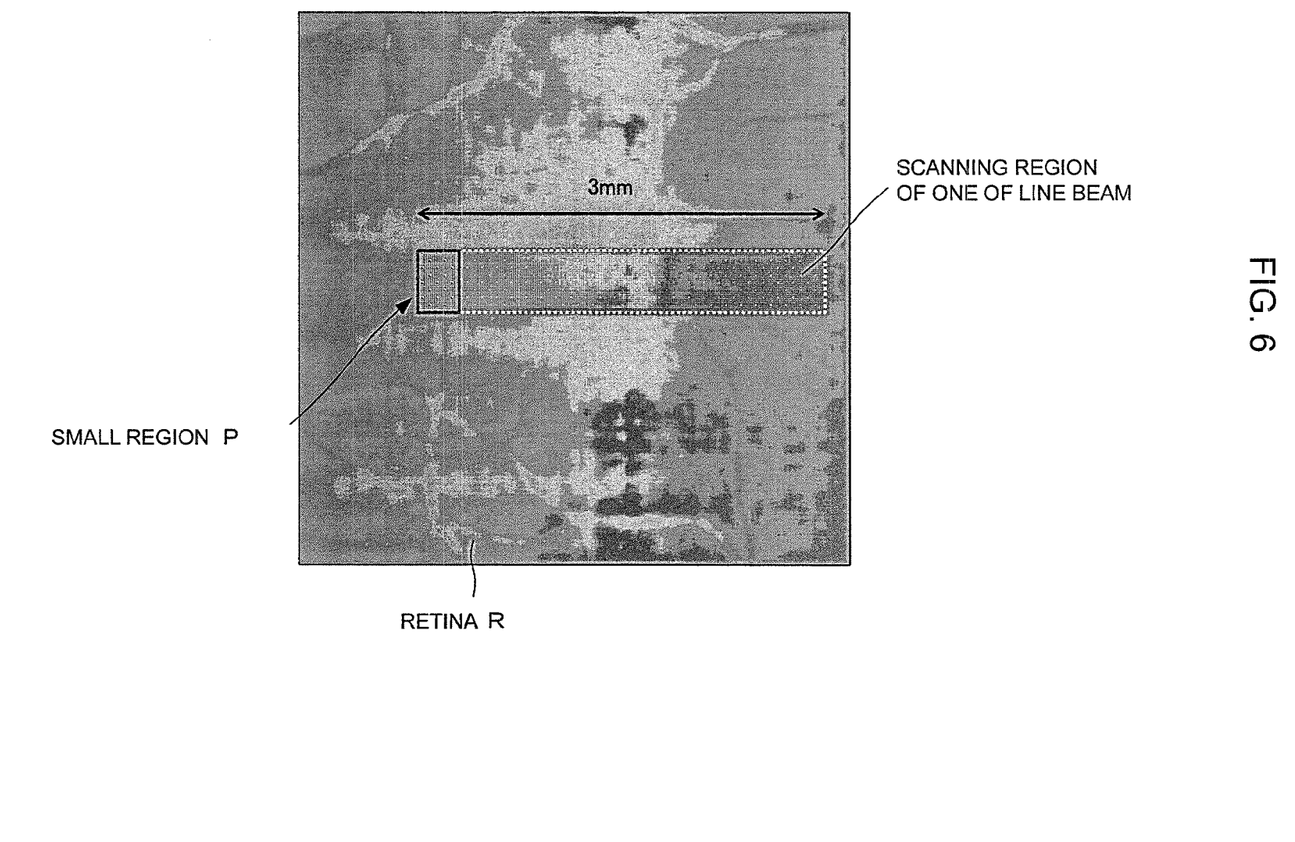
FIG. 6 is a diagram (part 1) for describing a detection principle for detecting scanning position displacement during scanning of a retina in an embodiment.
Figure 7:
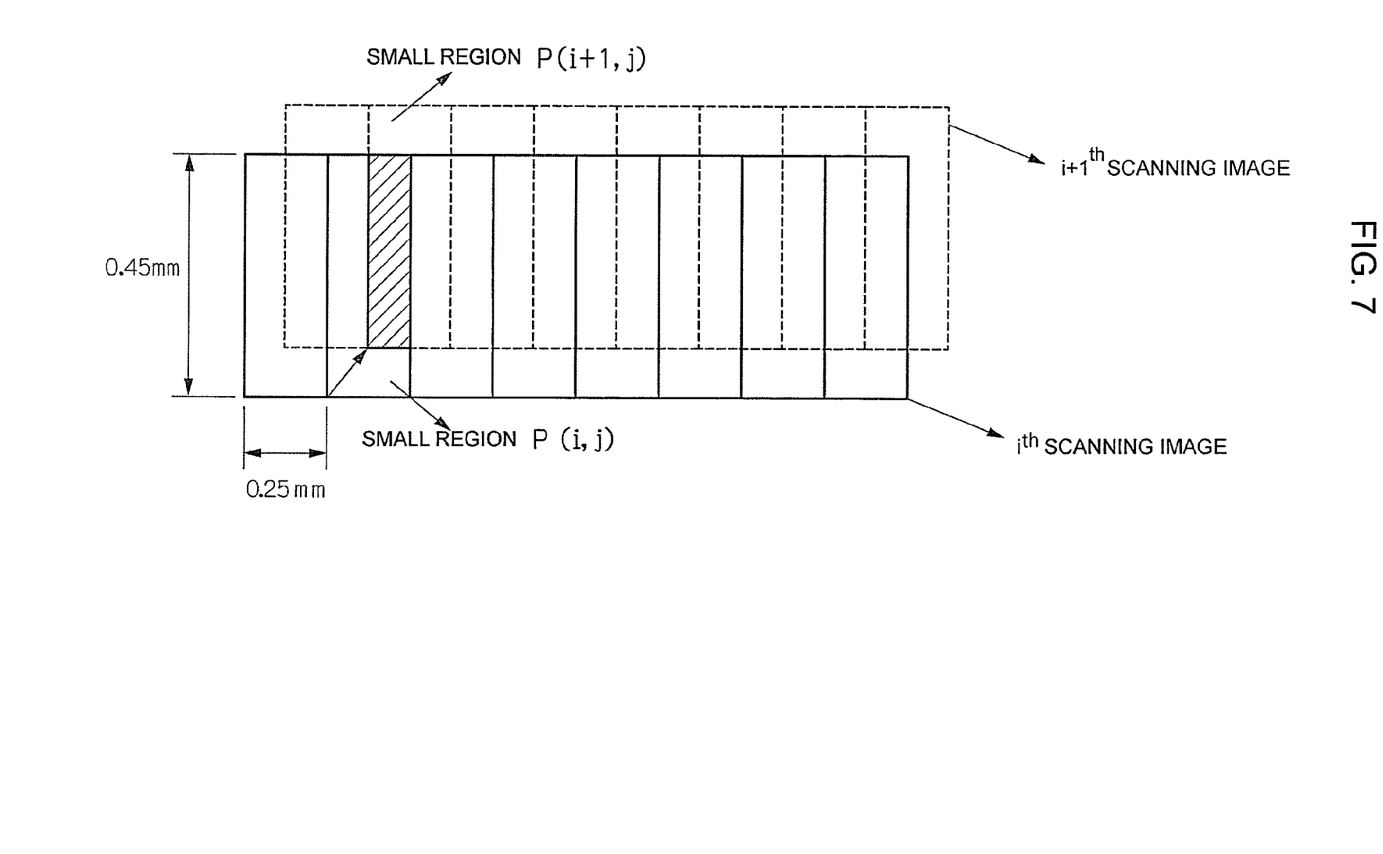
FIG. 7 is a diagram (part 2) for describing a detection principle for detecting scanning position displacement during scanning of a retina in an embodiment.

Subsequently, the detection principle for detecting the scanning position displacement during scanning of retina R and positional displacement detector 223 in the present embodiment will now be described using FIGS. 6 and 7. FIGS. 6 and 7 are diagrams for describing the detection principle for detecting the scanning position displacement during scanning of retina R in the present embodiment.

Usually, even when a subject intends to stop the movement of his/her eyes by fixing the gaze, his/her eyes constantly oscillate in a microscopic manner. The maximum amount of movement thereof over retina R is 100 μm and the maximum speed at that time is approximately 4 μm/ms. Accordingly, since retina R cannot be scanned, in a precise manner, through simple control alone of the scanning of retina R by the object scanning light in regard to two axes, i.e. in the width and longitudinal directions of retina R, it is necessary to detect the amount of scanning position displacement during scanning of retina R due to the movement of the eye.

For example, when the scanning interval of the object-scanning light beam in the longitudinal direction (the scanning interval of the sub-scanning) is assumed to be 6 μm, when retina R moves in the width direction (i.e. the x direction) by Δx and in the longitudinal direction (i.e. the y direction) by Δy, the scanning position displacement during scanning of retina R will be Δx μm in the x direction and (Δy+6) μm in the y direction.

Accordingly, in the present embodiment, in order to detect the scanning position displacement during scanning of retina R, irradiation of a line beam having a predetermined width (the length in the longitudinal direction of the detection region of retina R) is made for each interval, which is smaller than the scanning interval in the longitudinal direction of the object-scanning light beam, such interval being calculated from the spot diameter of the object-scanning light beam on retina R.

More specifically, by acquiring two images (tracking images), in which scan lines for the line beam are located next to each other, and which are obtained based on the line beam reflected from retina R (i.e. the line reflection beam described above) and then by calculating mutual correlation regarding the overlapping image region in such two images, the scanning position displacement (i.e. the positional displacement) during scanning of retina R arising from the eye movement can be calculated.

On the other hand, a predetermined time period is necessary for one scanning of the line beam, and thus, in order to obtain two images in which scan lines are located next to each other, a time period twice as long as such predetermined time period is necessary. More specifically, since the line beam interlocks with the object-scanning light beam and scans in the main scanning direction and also moves in association with the sub-scanning of the object-scanning light beam, a time period during which two scan lines are completed is necessary in order to obtain the two tracking images. Accordingly, when the movement distance of retina R, which can be converted from such time period, goes beyond the image resolution, the scanning position displacement during scanning of retina R cannot be removed even when the mutual correlation described above is calculated.

For this reason, despite the fact that it is necessary, when generating retinal images, to obtain and average a plurality of retinal images for one and the same position in order to reduce the influence of speckle noise (random noise) which occurs due to random interference between the object-scanning light beams, when such positional displacement occurs in the scanning position during scanning of retina R (i.e. when the displacement cannot be removed), consequently, the influence of speckle noise (random noise) cannot be reduced.

For example, as described above, in the case of the width of the inspection region of retina R being 3 mm, when a general scanning speed of 140 kHz is assumed, the time period necessary for one scanning of the object-scanning light beam is 3.57 ms. Thus, a time period of 7.14 ms, which is twice the time period necessary for such one scanning, is necessary in order to obtain an image from each of two line reflection beams of the neighboring scan lines. Accordingly, since the maximum speed at the time when retina R moves is approximately 4 μm/ms, the positional displacement during this time is approximately 30 μm.

In addition, when an object-scanning light beam having a wavelength of 780 nm, as described above, is used, spot diameter W of the object-scanning light beam on retina R can be calculated as 13 μm, as indicated in formula 6 below, based on the light diffraction theory, and thus, the resolution of the object-scanning light beam will be 13 μm. It should be noted that when the aperture of the device is assumed to be 3 mm and the diameter of the eye ball is assumed to be 20 mm, numerical aperture NA would be 0.0748 and when spot diameter W w is calculated using formula 6 by applying to such formula 6 a coefficient of 1.2 of the theoretical formula of diffraction, 13 μm is obtained.

$$\text{Spot Diameter } W = \frac{1.2 \times \text{Wavelength } \lambda}{\text{Numerical Aperture } NA} \qquad [\text{Formula 6}]$$

Accordingly, considering that the positional displacement that occurs due to the eye movement is 30 μm and the resolution of the scanning is 13 μm, when the scanning position displacement during scanning of retina R becomes larger than the resolution of the object-scanning light beam, the scanning position displacement during scanning of retina R cannot be calculated even when the mutual correlation described above is calculated.

Accordingly, in the present embodiment, as shown in FIG. 6, by dividing the image that is obtained from one line reflection beam into a plurality of small regions P with respect to the scanning direction of the relevant line beam (i.e. the width direction of retina R) and by calculating the mutual correlation of the overlapping image region for two images of the small region for one and the same position (position in the x direction) of two line reflection beams, the scan lines thereof being located next to each other, the scanning position displacement during scanning of retina R can be eliminated in real time based on such calculation result. In addition, when obtaining and averaging a plurality of retinal images for one and the same position, since alignment of the respective images can be performed, in a precise manner, consequently, it is possible to obtain a high-quality retinal image with a reduced influence of speckle noise (random noise) therein.

In particular, positional displacement detector 223 of the present embodiment generates an image of each line reflection beam in real time, divides the image obtained by each line reflection beam into a plurality of small regions P, with respect to the main scanning direction of the relevant line beam, calculates the mutual correlation of the overlapping image region with regard to two images of the small region P that belongs to one and the same position in the main scanning direction of the two line reflection beams, the scan lines of the line reflection beams being located next to each other, and then calculates the scanning position displacement during scanning of retina R based on the calculated mutual correlation of the image region.

For example, as shown in FIG. 7, positional displacement detector 223 divides the line reflection beam having, for example, a width of 0.45 mm and a wavelength of 700 nm into a predetermined number (for example, 12) of small regions P for every 0.25 mm in the width direction of retina R and makes use of the image in each of the divided small regions P (hereinafter referred to as a "small region scanning image").

In addition, positional displacement detector 223 detects an overlap between a small region scanning image of one small region P in the line reflection beam in one of the scan lines and a small region image in the small region P for one and the same position in the line reflection beam in a next scan line of the scan lines, calculates the mutual correlation in the detected overlap and then calculates the amount of scanning position displacement during scanning of retina R in both regions arising from the movement of retina R.

In other words, positional displacement detector 223 calculates, regarding the overlapping region in a small region scanning image of the $j^{th}$ small region P(i, j) out of 12 small regions P in line reflection beam N in the $i^{th}$ scanning, and in a small region scanning image of the $j^{th}$ small region P(i+1, j) out of 12 small regions P in line reflection beam N+1 in the i+1$^{th}$ scanning, the mutual correlation between each of the images.

It should be noted that a time period for obtaining the small region scanning image of the $j^{th}$ small region P(i, j) and the small region scanning image of the $j^{th}$ small region P(i+1, j) is 3.75 ms, which equals the time period for performing one scanning, and the scanning position displacement during scanning of retina R during such time period amounts to approximately 14 µm. This value is substantially equivalent to the resolution described above, and thus, the distortion in the image obtained in image detector 150 becomes negligibly small.

In addition, the divided small regions are not particularly limited; however, depending on the spot diameters of the line beam and the object-scanning light beam, the time for calculating the scanning position displacement during scanning of retina R, the detection capability or the like, the small region may require a size, in both longitudinal and width directions, of more than 100 µm, which is the maximum amount of scanning position displacement during scanning of retina R.

In addition, when the amount of the scanning position displacement during scanning of retina R is calculated in this way, positional displacement detector 223 outputs to controller 300 the instructions for controlling scanning mirror 146 based on the calculated positional displacement amount.

As described above, optical coherence eye-fundus tomography device 100 of the present embodiment can cause the object-scanning light beam and the line beam to propagate so as to provide irradiation to retina R using one and the same light path in inspection unit 140.

Accordingly, optical coherence eye-fundus tomography device 100 of the present embodiment can detect, in a precise manner, the scanning position displacement during scanning of retina R with a simple configuration, since it can make a light path of the beam for detecting the scanning position displacement during scanning of retina R identical with a light path of the beam for scanning retina R.

Moreover, optical coherence eye-fundus tomography device 100 of the present embodiment can perform, in a precise manner, alignment of the respective images when obtaining and averaging a plurality of retinal images for one and the same position, since it can detect, in a precise manner, the scanning position displacement.

Accordingly, optical coherence eye-fundus tomography device 100 of the present embodiment can obtain a high-quality retinal image with a reduced influence of speckle noise (random noise) therein, such noise occurring due to random interference between the object-scanning light beams.

In particular, as compared to the case in which the images by the line beam are obtained for the entire one scan line, optical coherence eye-fundus tomography device 100 of the present embodiment detect the scanning position displacement during scanning of retina R in a prompt manner, since it can detect the scanning position displacement during scanning of retina R as long as images of a relevant small region can be obtained.

In addition, optical coherence eye-fundus tomography device 100 of the present embodiment the scanning position displacement during scanning of retina R in a prompt manner, since it can detect the scanning position displacement during scanning of retina R using neighboring scanning lines of line beams.

Furthermore, in the present embodiment, scanning mirror 146 is used for the adjustment of irradiation positions of the line beam and the object-scanning light beam onto retina R; however, the present invention is not limited thereto, and any means may be used, as long as it can adjust the scanning positions of the line beam and the object-scanning light beam and also it can adjust the irradiation positions of the line beam and the object-scanning light beam onto retina R, based on the detected scanning position displacement during scanning of retina R.

Moreover, in the present embodiment, positional displacement detector 223 calculates the mutual correlation between the two images obtained by two line reflection beams, the scan lines thereof being located next to each other; however, the amount of scanning position displacement during scanning of retina R may be detected by using the line reflection beam in the first scan line as a reference and then by calculating the mutual correlation between two images obtained by the other line reflection beams, or the amount of scanning position displacement during scanning of retina R may be detected by calculating the mutual correlation between two images obtained by the line reflection beams, the scan lines thereof are not located next to each other, such as the $i^{th}$ line reflection beam and the i+2$^{th}$ line reflection beam and so on.

DESCRIPTIONS OF REFERENCE NUMERALS

BI Optical isolator
EY Eyeball
R Retina
RM Reflection mirror
100 Optical coherence eye-fundus tomography device
110 First light source unit
111 First irradiation source
112 Calibration section
120 Light distributing and coupling unit
121 Optical splitter/coupler
122 Second polarization controller
123 Conversion lens for light distributing and coupling unit
130 Reference light unit (reference light beam unit)
131 First polarization controller
132 First transformation lens
133 Achromatic lens
134 Water vial
135 Second transformation lens 140 Inspection unit
141 Forth polarization controller first
142 Forth polarization controller
143 Wavefront sensor
144 Prism for sensor
145 Deformable mirror
146 Scanning mirror
147 Second planar mirror
148 (148a, 148b) Concave mirrors
149 Third planar mirror
150 Image detector
151 Third polarization controller
152 Transformation lens for image detector
153 Grating section
154 Scanning camera
155 Image generator
156 Display
210 Second light source unit
211 Second irradiation source
212 Transformation lens for second light source unit
213 Cylindrical lens
220 Positional displacement detector
221 Line sensor
222 Transformation lens for positional displacement detector
223 Positional displacement detector
230 Dichroic mirror
240 Beam splitter
300 Controller

The invention claimed is:

1. A three-dimensional retina image generator, comprising:
  a first light source unit that has a first light source;
  a light divider that divides an output light beam output from the first light source into an object-scanning light beam that is delivered to a retina of an eye ball and a reference light beam for reference;
  a reference light beam unit, into which the reference light beam is input and that causes the input reference light beam to reflect as a reference reflection light beam;
  a measurement unit that scans the retina by the object-scanning light beam and that causes light scattered at the retina to reflect as an object-reflected light beam;
  an interference intensity detector that generates an interference light beam in which the reference reflection light beam and the object-reflected light beam are caused to interfere with each other and that detects an interference intensity for each wavelength in the generated interference light beam;
  a generator that generates a three-dimensional image of the retina based on the detected interference intensity for each wavelength;
  a second light source unit that has a second light source for outputting a line beam and that outputs the line beam in order to transmit the line beam in a path identical to that of the object-scanning light beam in the measurement unit; and
  a positional displacement detector that has a line sensor, that detects the line beam reflected from the retina and output from the measurement unit by the line sensor and that detects scanning position displacement during scanning of the retina by the object-scanning light beam based on the detected line beam,
  wherein the measurement unit includes:
    a light control mechanism that adjusts scanning positions when the line beam and the object-scanning light beam scan the retina; and
    a controller that performs control of the light control mechanism, and
  wherein the controller controls the scanning positions when the line beam and the object-scanning light beam scan the retina in the light control mechanism, based on the detected scanning position displacement.

2. The three-dimensional retina image generator according to claim 1, wherein
  the light control mechanism has a movable mirror, and the control section controls the movable mirror, based on the detected scanning position displacement, and controls the scanning positions when the retina is scanned with the object-scanning light beam and the line beam.

3. The three-dimensional retina image generator according to claim 1, wherein
  the positional displacement detector generates an image based on each line reflection beam, which is the reflected line beam, calculates mutual correlation between two images obtained by the corresponding line reflection beams and calculates the scanning position displacement during scanning of the retina based on the calculated mutual correlation.

4. The three-dimensional retina image generator according to claim 3, wherein
  the positional displacement detector divides each of the images obtained by the line reflection beams into a plurality of small regions with respect to the main scanning direction of a relevant line beam, calculates the mutual correlation regarding two images of a small region that belongs to one and the same position in the main scanning direction in the two images, and calculates the scanning position displacement during scanning of the retina based on the calculated mutual correlation.

5. The three-dimensional retina image generator according to claim 3, wherein
  the positional displacement detector calculates the mutual correlation of the overlapping image region with regard to two images of small regions that belong to one and the same position in the main scanning direction of two line reflection beams, the scan lines of the line reflection beams in the main scanning direction being located next to each other.

6. The three-dimensional retina image generator according to claim 1, wherein
  the line beam is a beam that extends in the sub-scanning direction of the object-scanning light beam.

7. The three-dimensional retina image generator according to claim 1, wherein
  a light control mechanism is a single mechanism.

* * * * *